United States Patent
Christie et al.

(10) Patent No.: US 9,625,408 B2
(45) Date of Patent: Apr. 18, 2017

(54) DETECTION METHOD AND APPARATUS FOR REDUCED CROSS-TALK AND ASIC AREA OF A FINGERPRINT SENSOR

(71) Applicant: IDEX ASA, Fornebu (NO)

(72) Inventors: Nicolai W. Christie, Hosle (NO); Geir Ivar Bredholt, Oslo (NO)

(73) Assignee: IDEX ASA, Fornebu (NO)

( * ) Notice: Subject to any disclaimer, the term of this patent is extended or adjusted under 35 U.S.C. 154(b) by 187 days.

(21) Appl. No.: 14/511,519

(22) Filed: Oct. 10, 2014

(65) Prior Publication Data

US 2015/0115981 A1  Apr. 30, 2015

(30) Foreign Application Priority Data

Oct. 28, 2013  (NO) .................................. 20131424

(51) Int. Cl.
*G01R 27/26* (2006.01)
*G01N 27/22* (2006.01)
*G06K 9/00* (2006.01)

(52) U.S. Cl.
CPC ......... *G01N 27/228* (2013.01); *G06K 9/0002* (2013.01)

(58) Field of Classification Search
CPC ........................ G01N 27/228; G06K 9/0002
USPC ....................................... 324/661, 663, 679
See application file for complete search history.

(56) References Cited

U.S. PATENT DOCUMENTS

| | | | |
|---|---|---|---|
| 6,055,324 A | 4/2000 | Fujieda | |
| 6,927,581 B2 | 8/2005 | Gozzini | |
| 7,084,642 B2 | 8/2006 | Gozzini | |
| 7,088,144 B2 | 8/2006 | Tang et al. | |
| 7,184,581 B2 * | 2/2007 | Johansen | G06K 9/0002 382/124 |
| 7,239,153 B2 | 7/2007 | Nysaether | |
| 8,041,083 B2 | 10/2011 | Pai et al. | |
| 2008/0069413 A1 | 3/2008 | Riedijk et al. | |
| 2012/0134549 A1 | 5/2012 | Benkley, III | |
| 2013/0181949 A1 | 7/2013 | Setlak | |
| 2013/0249855 A1 | 9/2013 | Zhang | |

FOREIGN PATENT DOCUMENTS

WO  WO 2004077340 A1  9/2004

OTHER PUBLICATIONS

International Search Report issued in International Application No. PCT/EP2014/073056, 3 pages (Mar. 6, 2015).

(Continued)

*Primary Examiner* — Farhana Hoque
(74) *Attorney, Agent, or Firm* — Rothwell, Figg, Ernst & Manbeck PC

(57) ABSTRACT

A method and apparatus for electrical detection of a finger print has a reduced number of interconnect signals between a sensor area and a substrate and an electronic circuit for excitation and detection of the finger print compared to a single-chip finger print sensor. The individual signals are connected internally at the sensor substrate in such a way that the response from the individual sensor elements can be separated from each other. Cross-talk is reduced by keeping the sensor outputs at a constant potential, thus eliminating the effect of capacitive coupling between different sensor outputs and also between sensor outputs and a ground or reference potential.

12 Claims, 10 Drawing Sheets

(56) References Cited

OTHER PUBLICATIONS

Written Opinion issued in International Application No. PCT/EP2014/073056, 6 pages (Mar. 6, 2015).
Search Report issued in Norwegian Patent Application No. 20131424, 2 pages (May 27, 2014).
International Preliminary Report on Patentability for International Application PCT/EP2014/073056 dated Feb. 1, 2016, 15 pages.

* cited by examiner

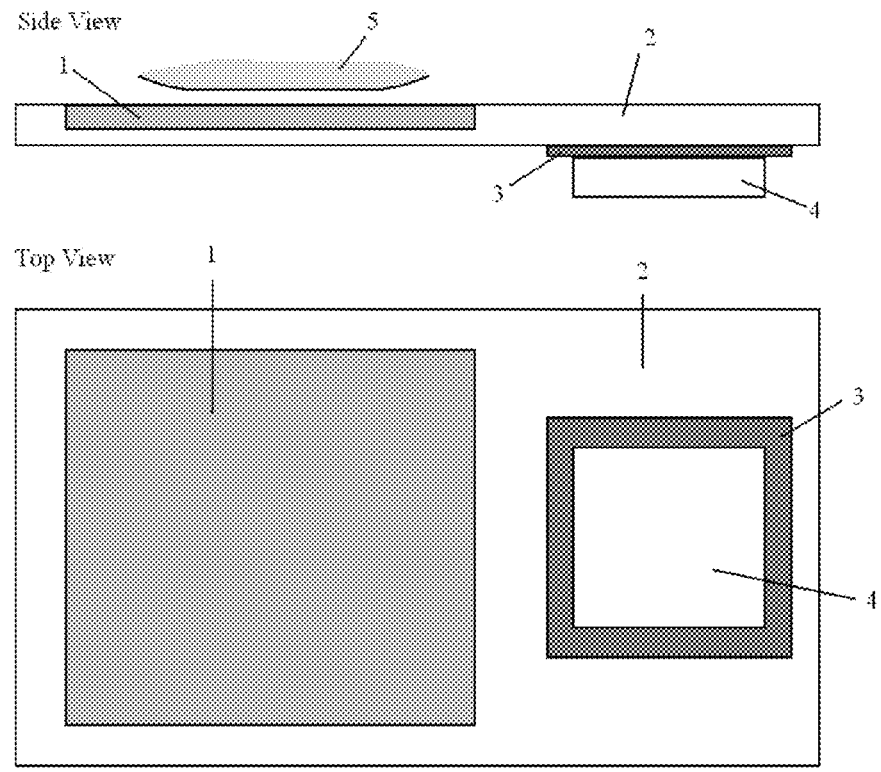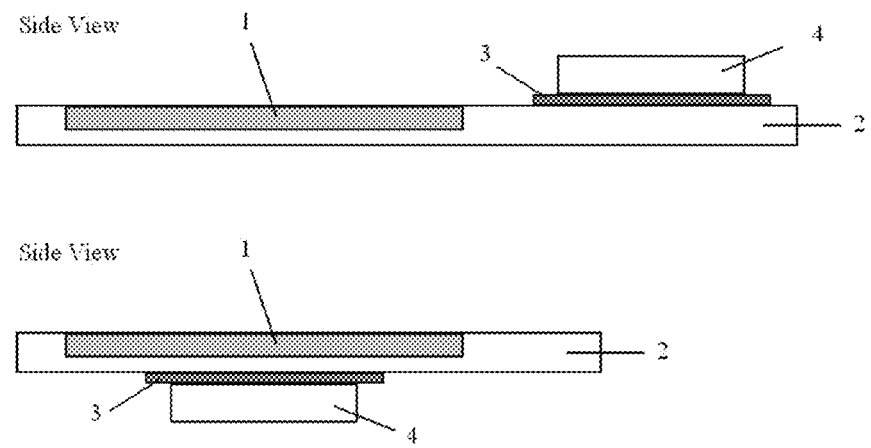

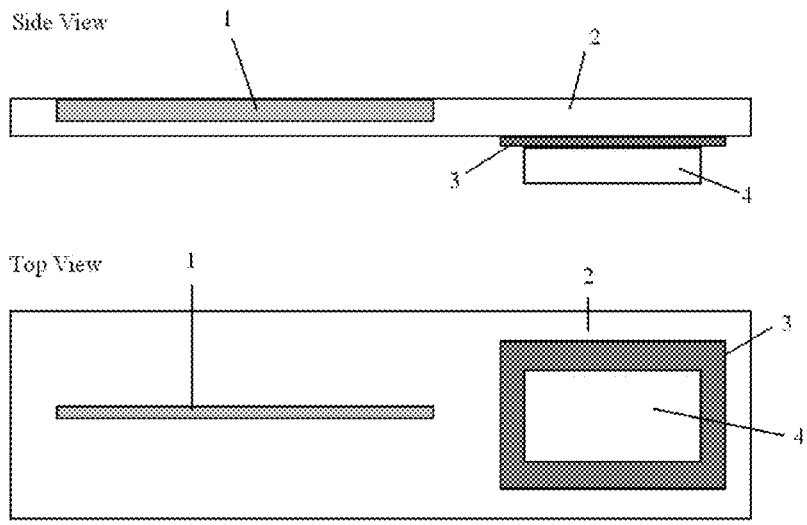
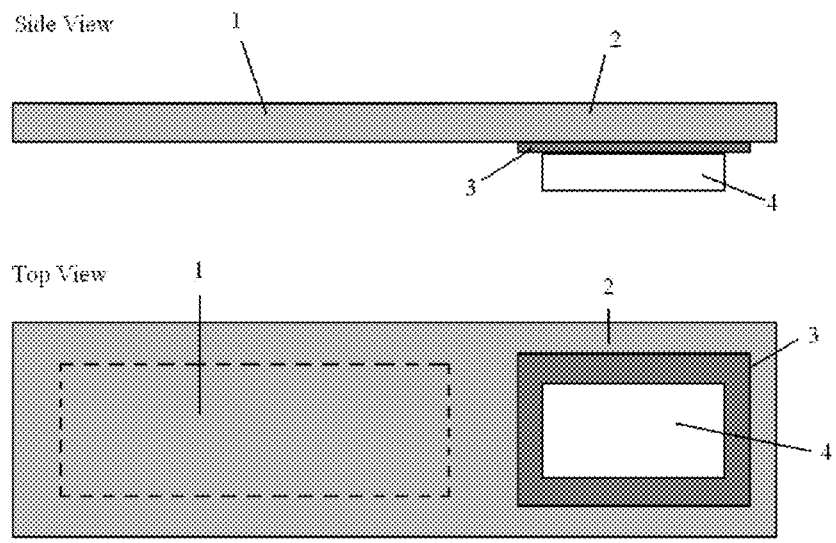

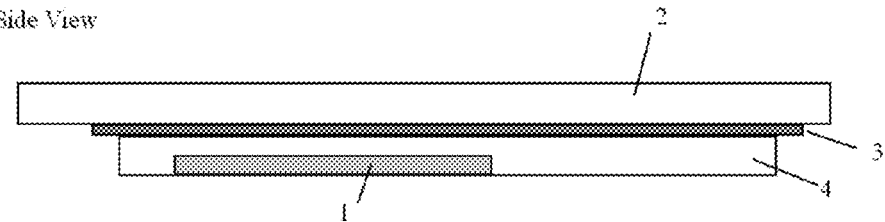
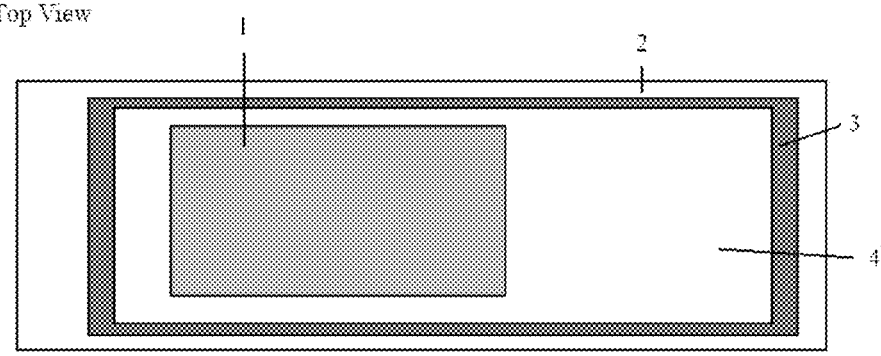
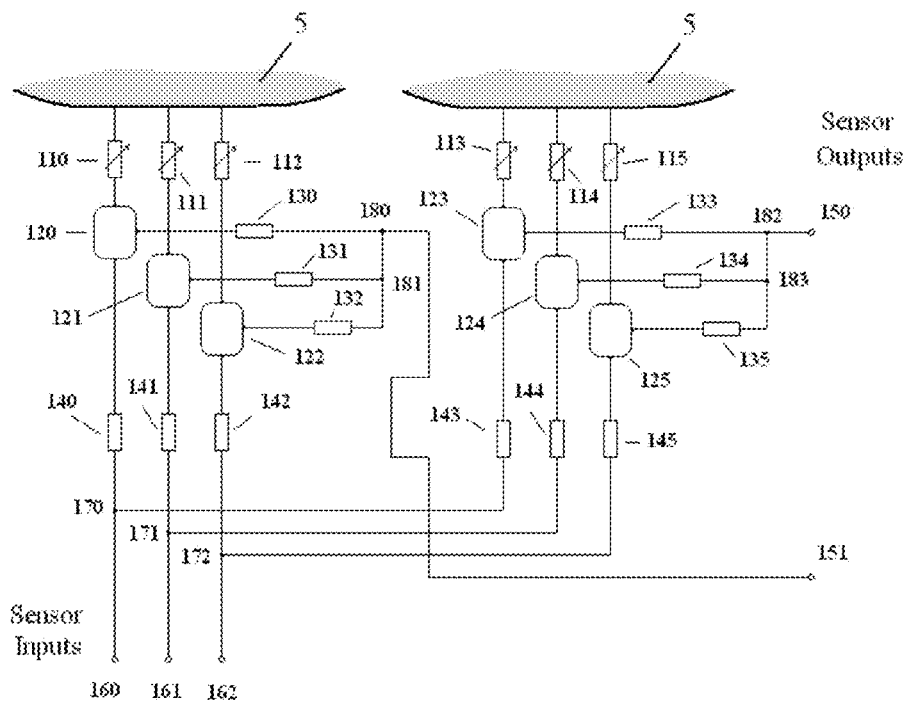

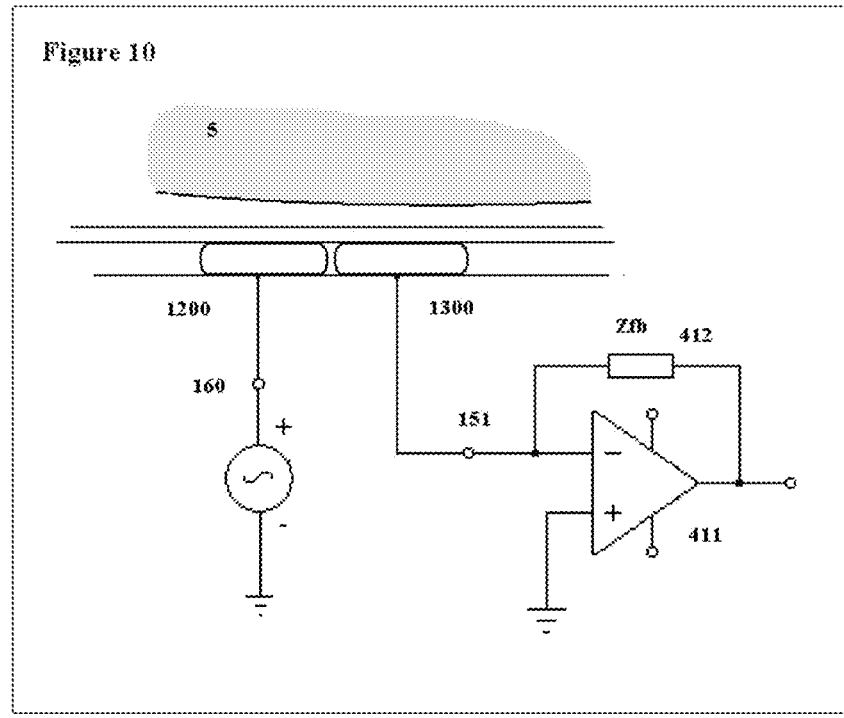
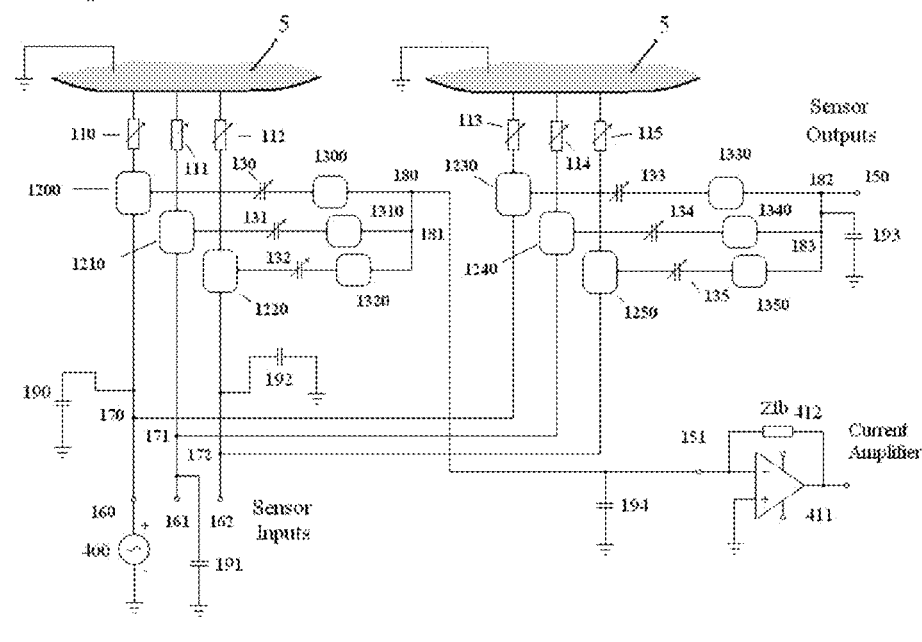

DETECTION METHOD AND APPARATUS FOR REDUCED CROSS-TALK AND ASIC AREA OF A FINGERPRINT SENSOR

CROSS REFERENCE OF RELATED APPLICATION

This application claims the benefit under 35 U.S.C. §119 of the filing date of Norwegian patent application No. 20131424 filed Oct. 28, 2013, the disclosure of which is incorporated herein by reference.

BACKGROUND OF INVENTION

Today there is an increasing demand for low cost finger print sensor devices for biometric authentication based on finger print recognition. However, since the cost of a finger print sensor often is proportional to the area of the sensor, and since the area of the sensor needs to be comparable to the dimensions of the finger, it is not trivial to bring down the cost of silicon based finger print sensors sufficiently; this is true especially for area sensors.

However, one way to solve this is to implement the detection electrodes in a separate and completely or at least partly passive Sensor Substrate, which can be made out of other materials and processes than single-crystalline silicon needed for electronic circuits. In this way a potential lower-cost of such a passive or partly passive Sensor Substrate can be utilized for obtaining an overall cost-efficient solution combining a low cost Sensor Substrate with a relatively smaller electronic (interface) circuit.

In such a configuration the Sensor Substrate can have a size matching the dimensions of the finger and it is this possible to combine this with an Electronic Circuit of significantly smaller dimensions and correspondingly lower cost than what would be the cost of an Electronic Circuit with essentially the same dimensions as the finger.

However, although the overall cost of the components of such a finger print sensor, consisting of a Sensor Substrate and an Electronic Circuit can be significantly lower than a corresponding solution based on a single-chip solution, the cost of assembling the two parts will increase the cost of the finished finger print sensor, in spite of the continuously reduced cost levels of such assembly processes in volume manufacture of today.

One important cost factor is related to the electric connections between such a Sensor Substrate and the Electronic Circuit. The cost of such interface connections is normally proportional to the actual number of interface connections. One way to reduce the cost of the interface connections is thus to reduce the number of interface signals.

Additionally, on the electronic circuit there is also a cost associated with every interface signal, since every signal requires a minimum connection area, which normally cannot be utilized for other functions. Thus if the number of interface signals between the electronic circuit and the Sensor Substrate can be reduced, the cost of the electronic circuit can also be reduced.

SUMMARY OF THE INVENTION

It is an objective of the present invention to provide a method and apparatus for electrical detection of a finger print or other physical, chemical or thermal characteristics of a finger with a significantly reduced number of interconnect signals between a Sensor Area and (separate low cost passive Sensor Substrate) and an Electronic Circuit for excitation and detection of the finger print or other physical characteristics for area and cost saving compared to a single-chip finger print sensor. This is obtained by internally electrically connecting the individual signals internally at the sensor substrate but in such a way that the response from the individual sensor elements can be separated from each other. This is furthermore obtained by utilizing a current sensing detector which makes sure that other sensor elements and their electrical coupling to the finger do not interfere with the sensor element or sensor elements that is or are currently detected.

Another object of the present invention is to provide a method and an apparatus for detection of a finger print with reduced cross-talk, as a way to obtain improved image quality and contrast, which also improves overall biometric performance of the finger print sensor. The cross-talk is reduced by keeping the Sensor outputs which outputs are connected to individual sensor elements at a constant potential, thus eliminating the effect of capacitive coupling between different sensor outputs and also between sensor outputs and a ground or reference potential.

Another object of the present invention is to provide a method and an apparatus for detection of a finger print or other physical characteristics of a finger based on measuring and detection of the signal from a plurality of sensor elements at the same point in time, which is enabled by having a greatly reduced cross-talk between the individual sensor outputs.

Another object of the present invention is to provide a method and an apparatus for detection of a finger print with reduced dependency of parasitic capacitances of the Sensor Substrate and thus obtain a more uniform sensor gain or attenuation across the width or area over or along which the Sensor Elements are located.

Another object of the present invention is to provide a method and an apparatus for detection of a finger print or other physical characteristics of a finger with an increased sensitivity to the response signal from the finger by implementing a current sensitive detector where the voltage on the sensor inputs is kept constant, so that the response signal from the finger is not attenuated (to a varying degree) by varying parasitic capacitances across the sensor substrate, since no current will flow into these parasitic capacitances as long as the voltage is kept constant.

Another object of the present invention is to provide a method and an apparatus for reduced number of input and outputs/electronic connections between the Sensor Substrate and an electronic circuit as a way to obtain a reduced cost of a finger print sensor (or sensor for detection of other physical or chemical characteristics of the finger without reducing the biometric performance of the finger print sensor.

Another object of the present invention is to provide a method and an apparatus for a two-dimensional fingerprint sensor with a strongly reduced number of interface connections between the Sensor Substrate containing a number of Sensor Elements and the electronic circuit in relation to the total number of Sensor Elements (or pixels) of the Sensor Area (1).

BRIEF DESCRIPTION OF THE DRAWINGS

FIG. 1 shows one exemplary embodiment of a sensing system according to the present invention.

FIG. 2 shows an alternative arrangement of the sensing system according to the present invention.

FIG. 3 shows an alternative, essentially linear sensor geometry of the Sensor Area according to the present invention.

FIG. 4A shows an alternative arrangement of the sensing system according to the present invention.

FIG. 4B shows an alternative arrangement of the sensing system according to the present invention.

FIG. 5 is a schematic illustration of a Sensor Area including six Sensor Elements.

FIG. 10 shows an exemplary cross section for a sensor configuration with missing Sensor Element, including Excitation Element, Sensing Element as well as excitation and detection means according to the present invention.

FIG. 11 is a schematic illustration of a Sensor Area for a sensor configuration with missing Sensor Elements but including Excitation Elements, Sensing Elements along with Parasitic Output Capacitances of the Sensor Area as well as excitation and detection means according to the present invention.

DETAILED DESCRIPTION OF THE INVENTION

Figure 6:
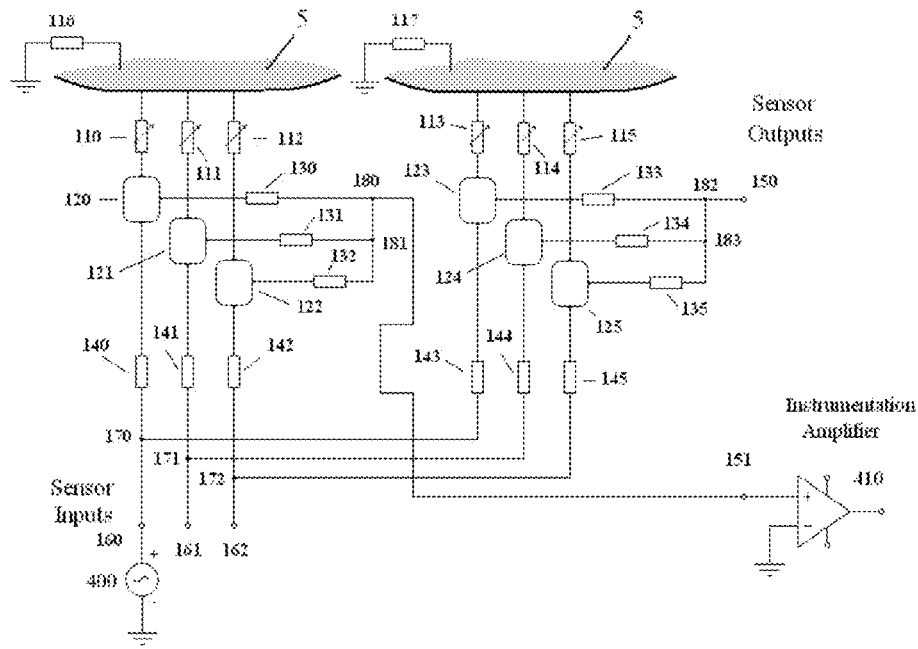
FIG. 6 is a schematic illustration of a Sensor Area including six Sensor Elements and excitation and prior art detection means (method).

FIG. 1 shows one exemplary embodiment of the invention consisting of a Sensor Area (1) arranged for having contact with a (partially shown) Finger (5) and with means (not shown) like sensor electrodes, for sensing physical characteristics of the finger, like the surface structure and the finger print of the finger. Furthermore, the embodiment comprises an Electronic Circuit (4) being electrically connected to the Sensor Area (1) and also the sensing means, for detection of physical characteristics the finger, surface structure as well as the finger print of the finger. Both the Sensor Area (1) as well as the Electronic Circuit (4) are supported by a Carrier (2) which also provides electrical connection between the Electronic Circuit (4) and the Sensor Area (1). The Carrier (2) can also physically be an integral part of the Sensor Area (1). The Electronic Circuit (4) is electrically connected to the Carrier (2) and the Sensor Area (1) and the sensing means (not shown) by a Connection Means (3) for the case that the Carrier (2) is not an integral part of the Electronic Circuit (4).

FIG. 2 shows an alternative arrangement of the Electronic Circuit (4) in relation to the Sensor Area (1).

FIG. 3 shows an alternative geometry of the Sensor Area (1), being essentially a line sensor.

FIG. 4A shows an alternative arrangement of the Sensor Area (1), where the Sensor Area (1), is essentially an integral part of the Carrier (2).

FIG. 4B shows an alternative arrangements of the Carrier (2) where the Carrier (2) is essentially an integral part of the Electronic Circuit (4) containing at least one active electronic device like a transistor, a transmission gate, a switch or another controllable electronic device.

FIG. 5 shows a general embodiment of the invention, for illustration purposes. More specifically, it illustrates the details of the Sensor Area (1). The Sensor Area (1) consists of a group of Sensor Elements (120, 121, 122) located in specific positions within the Sensor Area (1) and another group of Sensor Elements (123, 124 and 125) located somewhere else on the Sensor Area (1), so that the figure shows a total of 6 Sensor Elements.

The Sensor Elements have an electrical coupling to a Finger (5) which is located in proximity of the Sensor Area (1). This electrical coupling, or interaction, to the finger is depicted as Finger Impedances (110, 111, 112, 113, 114 and 115) (that is, impedances between the Finger (5) and the Sensor Elements (120-125) which model this electrical coupling or interaction. These Finger impedances are thus meant to represent so-called "lumped parameter" models of the actual (physical and) electrical interaction between the Finger (5) and the Sensor Elements (120-125).

An alternative way to depict this electrical coupling between the Sensor Elements and the Finger (5) could be a drawing of the electrical field lines between the Sensor Elements and the Finger (5). However, as a person skilled in the art would observe, for each specific geometry of the Sensor Element and the Finger (5) there always exists one lumped parameter model that describes in a complete (and detailed) way the precise properties of such an electrical coupling or interaction—by a position dependent (possibly also frequency dependent) Finger Impedance (110-115) as shown in FIG. 5. (By position dependent is meant Finger Impedances (110-115) being dependent on the relative difference in position between the Sensor Elements and the position of the Finger (5)).

By this we have thus established that for any detailed embodiment of the Sensor Elements there exists an equivalent lumped parameter model that accurately models the electrical coupling between the Sensor Elements (120-125) and the Finger (5), in this invention referred to as Finger Impedances (110-115).

These Finger Impedances will, as would be obvious for a person skilled in the art, vary depending on the finger condition like humidity and other physical characteristics, but also vary depending on the detailed ridge structure of the finger and thus the finger print, only given that the geometry and dimensions of the Sensor Elements are appropriate or comparable to the dimensions of the finger print of the Finger (5) so that adequate spatial resolution is obtained. This variation in properties is illustrated with an arrow crossing the Finger Impedances (which is a common way to indicate such variability).

As a person skilled in the art furthermore would observe, it is furthermore obvious that the geometry of the interface between the Finger (5) and the Sensor Elements (not shown) in all other respects should be arranged for giving sufficiently spatial resolution to enable for adequate representation of a finger print or other physical characteristics of the Finger (5) that are going to be detected across the Sensor Area (1).

As also shown in FIG. 5 the Sensor Area (1) furthermore accommodates Sensor Inputs (160, 161 and 162) as well as Sensor Outputs (150 and 151), which thus constitute an interface to the Electronic Circuit (4).

As also shown in FIG. 5 the Sensor Area (1) furthermore intentionally contains series impedances, like the Output Impedances (130, 131, 132, 133, 134 and 135) as well as the Input Impedances (140, 141, 142, 143, 144 and 145). The purpose of these Input and Output Impedances will become obvious in the following description of this invention. These Output and Input Impedances can in principle also be part of the Carrier (2), if this is convenient for other reasons, like cost or assembly related perspectives, Furthermore the Sensor Area (1) contains electrical Input Connections (170, 171, 172) between the Sensor Inputs and the individual Sensor Elements (via the Input Impedances (140 and 143, 141 and 144 as well as 142 and 145) as well as electrical Output Connections (180, 181, 182, 183) between Sensor Outputs and the individual Sensor Elements (via the Output Impedances (130, 131 and 132 as well as 133, 134 and 135).

As can be observed, it is these Output and Input Connections that permit reducing the number of Sensor Inputs and Sensor Outputs according to this invention, as long as the Input or Output Impedances are part of the low cost Sensor Area (1) or possibly another low-cost Carrier (2) attached to the Sensor Area (1).

As explained above, FIG. 5 is meant for illustration purposes only, which means that the number of Sensor Inputs and Sensor Outputs in a real finger print sensor design for a given implementation will be determined by the specified geometry and resolution of Sensor Area (1). It is furthermore shown in FIG. 5) that the three Sensor Inputs are connected electrically together while the only two Sensor Outputs are connected electrically together. However, this may also be reverse and finally determined by the given implementation, like the number of Sensor Inputs and Sensor Outputs described above.

FIG. 5 furthermore shows that a total of six Sensor Elements are detected by a total of five Sensor Inputs and Sensor Outputs, as opposed to traditional finger print sensors which normally would contain a total of at least six Sensor Outputs, one for each Sensor Elements. This illustrates the benefit of the present invention, although not on a large scale.

On a large scale, this detection principle will in general allow for detection of Nin times Nout Sensor Elements, where Nin is the number of Sensor Inputs and Nout is the number of Sensor Outputs. Thus the total number of Sensor Inputs and Sensor Outputs Ntot goes as a linear function of these two variables:

$$Ntot = Nin + Nout$$

while the total number of Sensor Elements SEtot goes as the product of the two variables:

$$SEtot = (Nin)(Nout)$$

and thus increases a lot faster than the Ntot. In other words, the savings in terms of total number of Sensor Inputs and Outputs increases with the total number of Sensor Elements, and would thus represent significant savings in IO—complexity of Line or Area Sensors.

As the observant reader will realize, the highest benefit from the described detection scheme in terms of number of Sensor Elements in relation to Sensor Inputs and Outputs would be when Nin=Nout. However, other relations between Nin and Nout will normally also yield significant reduction in the number of Sensor Inputs and Outputs.

Analyzing FIG. 5 further, we observe that addressing and detection of individual Sensor Elements (120-125) would require selecting and detecting the signal from one Sensor Output (150, 151) and furthermore activating only one Sensor Input (160, 161 or 162) at a time.

Analyzing the situation further, let us assume as a particular example that Sensor Input (160) and Sensor Output (151) are selected, although whichever other combination of Sensor Input and Sensor Output would be equivalent in analyzing the functionality of the detection principle of the present invention.

As an example, let us also furthermore assume for the purpose of illustration, that the Finger (5) represents electrical ground potential, as depicted in FIG. 6.

Analyzing FIG. 6 further, as an example, let us furthermore assume that the Sensor Input (160) is excited by a varying voltage from a Voltage Source (400)—with zero internal series resistance—and that the Sensor Output (151) connected to an Electronic Circuit (4)), furnished by an Instrumentation Amplifier (410) with (for the sake of simplicity of this example) infinite input impedance. The Instrumentation Amplifier (410) thus detects the voltage of the Sensor Output (151) relative to electrical ground potential.

As an experienced person skilled in the art would observe, the signal from the Voltage Source (400) will produce an electrical potential or voltage at the Sensor Element (120) which, in addition to be proportional to the magnitude of the Voltage Source (400) also will be proportional to the so-called voltage divider formed between the Input Impedance (140) and the Finger Impedance (110).

For this to be true we also assume for the moment no parasitic impedances in the Sensor Area (1) and that the Finger (5) represents electrical ground potential which for the moment is also the same as the electrical ground of the Voltage Source (400) the and Instrumentation Amplifier (410). (We furthermore need to assume that the impedance between the Finger (5) electrical ground (116) and (117) is low compared to the impedances (110) and (140), which usually also would is true.)

This basic detection principle would thus according to the above yield a voltage at the Sensor Element (120) which is proportional to the Finger Impedance (110) when the Sensor Input (160) and Sensor Output (151) are selected. Analyzing this further, a person skilled in the art would also observe that Sensor Inputs (161) and (162) should preferably be left open (or high-impedant) in order to avoid the signal at Input Connections (171, 172) to interfere with the signal at Output Connection 180 and 181 via the Input Impedances (141, 142) and the Output Impedances (131, 132).

We furthermore observe that the Input Impedances (140-145) provide that no Sensor Element is shorted together at the excitation side. If the Input Impedances (140-145) were not present, the electrical voltage at the Sensor Elements 120 and 123, as well Sensor Elements (121, 124) and Sensor Elements (122, 125) would be equal and there would be no way to distinguish the signals from the individual Sensor Elements (120-122) or Sensor Elements (123-125) from each other.

Based on the description related to FIG. 6 above we have thus established that the signal level from the Sensor Element (120) at the Sensor Output (180, 151) in addition to being proportional to the magnitude of the Voltage Source (400) also will be proportional to the so-called voltage divider formed between the Input Impedance (140) and the Finger Impedance (110), given no interference from the Sensor Elements of the same group (121, 122).

However, as a person skilled in the art would observe the signal at the Sensor Output (150, 151) can still be affected by the Finger Impedances (111, 112) through the connection (181) and the Output Impedances (131, 132) which represent alternative paths to ground. Thus the contact condition at the Sensor Elements (121, 122) will thus affect the signal at Output Connection (180) and thus the Sensor Output (151) in spite of the fact that the Sensor Inputs (171, 172) are deactivated. This means that cross-talk between the Sensor Element (120), and the Sensor Elements 121 and 122 will occur, in that the Sensor Output signal detected at the Sensor Output (150) by the Instrumentation Amplifier (410) will be influenced by the Finger Impedances (111, 112), not only the Finger Impedance (110) which is the one that is supposed to be measured.

The cross-talk situation described above will not be significantly changed by driving the Sensor Input (170) with an ideal current source (instead of an ideal voltage source). This is due to the fact that the current will immediately be converted to voltage due to the Finger Impedance (110), which acts as a shunt resistor that converts the current into a voltage.

However, one change at the Sensor Outputs can alter the cross-talk situation between the Sensor Element (120) and the Sensor Elements (121-122) described above.

Figure 7:
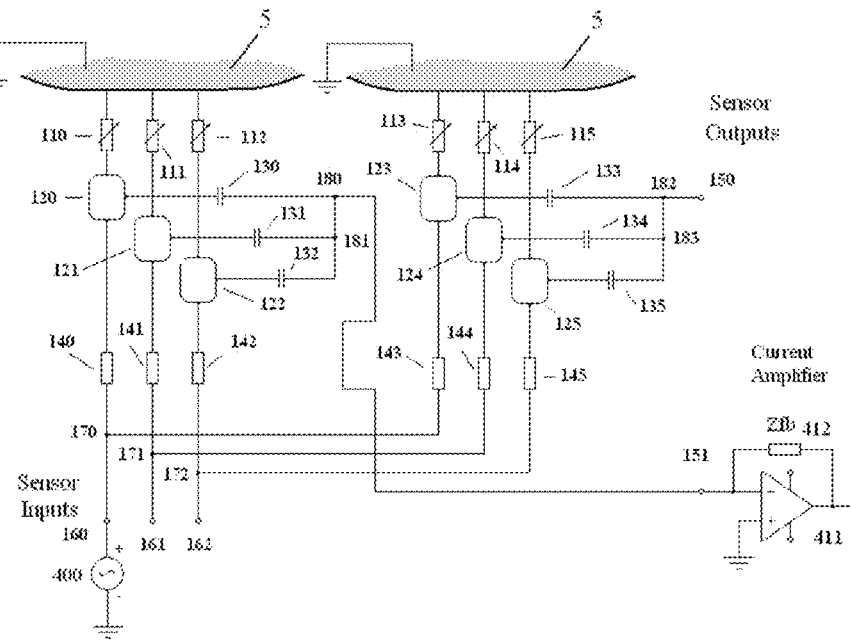
FIG. 7 is a schematic illustration of a Sensor Area including six Sensor Elements and excitation and detection means according to the present invention.

As an example let us for a moment assume that (both the Input Impedances (140-145) as well as) the Output Impedances (130-135) are essentially capacitive, as shown in FIG. 7.

As is furthermore shown in FIG. 7, assume that instead of an Instrumentation Amplifier 410 a Current Amplifier (411) is connected to the Sensor Output (151). In this example the Sensor Inputs (161, 162) can be open circuit as shown in the figure or they can be shorted to ground (not shown). In any case this will not basically influence on the operation described in FIG. 7.

Analyzing FIG. 7 further, the Current Amplifier (411) will amplify the currents from the Sensor Element (120) as they flow through the Output Impedance (130). However, due to the feedback mechanism and the Feedback Impedance Zfb (412) of such a current amplifier the voltage at the Sensor Output (151) will (within the bandwidth of the amplifier) be kept at a constant potential. (For the situation in FIG. 7 this potential will be ground since the positive input of the Current Amplifier (411) is connected to ground). This is a general property of all current amplifiers implemented in the described way and thus also the background for the notion that such an amplifiers generate "virtual ground" at the (negative) input terminal of the amplifier. In other words, the voltage at the negative input terminal, or the Sensor Output (151) remains at a constant electrical potential—independently of the current that flow towards this node.

Due to this fact, the voltage potential at Output connections (180, 181) is also kept constant and we observe furthermore that the voltage across the Output Impedances (131, 132) will also be constant—as long as the potential of the Finger (5) is constant. Since the current through a capacitor is dependent on the time derivative of the voltage across the capacitor, the current through the Output Impedances (131, 132) will therefore also be zero. Due to this fact we observe that the current that flows into the Current Amplifier (411) is solely dependent on the voltage potential of the Sensor Element (120) and thus the Finger Capacitance (110), and does not depend on the Finger Impedances (111, 112). Thus no cross-talk occurs between the signal at the Sensor Element (120) and the Sensor Elements (121, 122).

Figure 8:
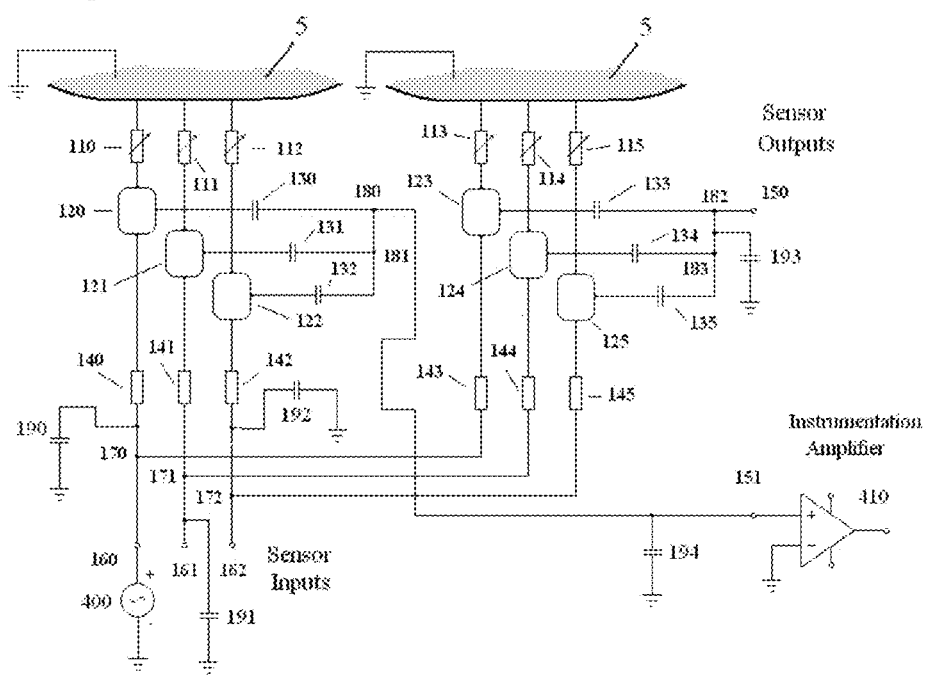
FIG. 8 is a schematic illustration of a Sensor Area including six Sensor Elements, excitation and prior art detection means, including Parasitic Output Capacitances of the Sensor Area.

In addition to the described improved cross-talk properties of the present invention, also in one other respect the current invention is favorable, as depicted in FIG. 8. FIG. 8 shows the Sensor Output (151) equipped with an instrumentation amplifier, to illustrate this.

FIG. 8 furthermore shows various so-called parasitic capacitances, which normally will occur in any given sensor implementation. The Parasitic Input Capacitances (190, 191, 192) model the capacitances that form between the Sensor Inputs (160, 161, 162) and the associated wiring to electrical ground. Furthermore, the Parasitic Output Capacitances (193, 194) model the capacitances that form between the Sensor Outputs (150, 151) and the associated wiring to electrical ground.

With regards to the Parasitic Input Capacitances (190-192) these will normally not affect sensor performance significantly, they will normally only load the Voltage Source (400) and cause an increase of the current that flows into the Sensor Inputs (160 to 162) and thus increase the overall current consumption, but the detected signal level at the Sensor Outputs (150, 151) will not be affected to any significant degree by these Input Capacitances (190-192).

With regards to the Parasitic Output Capacitances (193, 194) the situation is however different. For even a small line sensor these capacitances can be significant compared to the impedances of the Input Impedances (140-142) and the Output capacitors (130-132). Since the parasitic Output Capacitances (194) forms a voltage divider in conjunction with the Output Capacitance (130) the attenuation will therefore increase and the signal level will decrease as the parasitic Output Capacitance (194) increases.

Furthermore the attenuation and thus signal level at the Sensor Outputs (150) and (151) will be different from each other when there is a difference between the parasitic Output Capacitances (193, 194), causing non-uniformity with respect to Sensor attenuation or gain between different Sensor Outputs (150, 151), under otherwise equal conditions.

Figure 9:
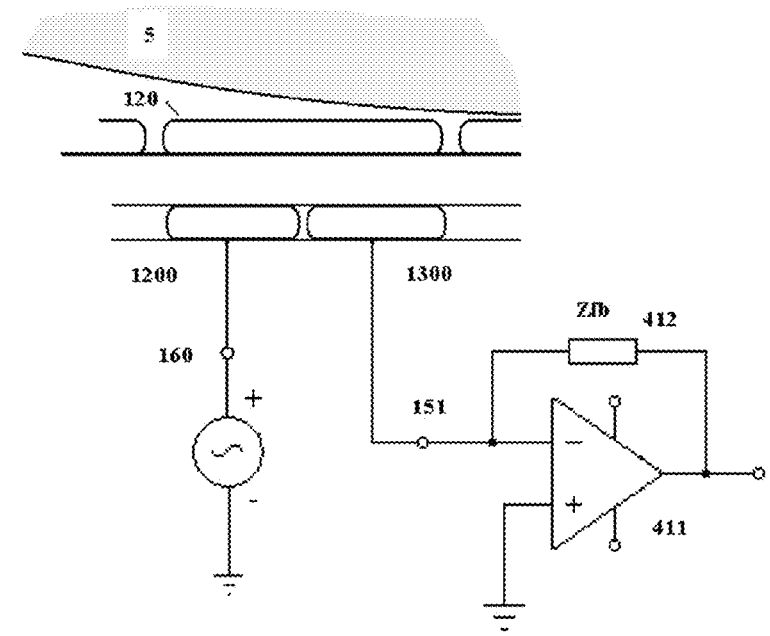
FIG. 9 shows an exemplary cross section including Sensor Element, Excitation Element and Sensing Element as well as excitation and detection means according to the present invention.

Considering FIG. 9, where the Sensor Output (151) is equipped with a Current Amplifier (411) this situation is different. Since the Current Amplifier keeps the voltage potential at the Sensor Output (151) at a constant level, no current will flow through the parasitic Output Capacitance (194). In this way the parasitic Output Capacitance (194) cannot affect the sensor attenuation and will furthermore not affect the signal level at the Sensor Output (151).

In the same way differences in the parasitic Output Capacitance (193, 194) for different Sensor Outputs cannot cause non-uniformity with respect to Sensor attenuation or gain between different Sensor Outputs (150, 151) as opposed to the description of FIG. 8, where the Sensor Output (154) is equipped with an instrumentation amplifier.

FIG. 9 shows schematically one way the described sensor structures can be implemented in a layered structure, including only one Sensor Element, for clarity. The Sensor Element (120) is placed at the side closest to the surface where the Finger (5) is located. The Sensor Element (120) can be covered with a protective layer, or it may be exposed directly to the finger. The Finger Impedance (110) (not shown) is formed as a result of the electric interaction and the electric fields flowing between the Sensor Element (120) and the Finger (5).

An Excitation Element (1200) positioned beneath the Sensor Element (120) so that an impedance (not shown) is formed as the result of the electrical interaction between the Sensor Element (120) and the Excitation Element (1200). In the same fashion a Sensing Element (1300) is positioned beneath the Sensor Element (120), so that an impedance (not shown) is formed as the result of the electrical interaction and the electrical fields flowing between the Sensor Element (120) and the Sensing Element (1300).

As can be understood by a person skilled in the art this basic sensing structure can be implemented in many different ways without departing from the basic detection principle described above.

Another way to implement this detection principle is shown in FIG. 10. In this configuration the Sensor Element (120) is simply removed. The Excitation Element (1200) is positioned beneath the Finger (5) so that an impedance (not shown) is formed as the result of the electrical interaction between the Excitation Element (1200) and the Finger (5). In the same fashion the Sensing Element (1300) is also positioned beneath the Finger (5) so that an impedance (not shown) is formed as the result of the electrical interaction and the electrical fields flowing between the Sensing Element (1300) and the Finger (5).

However, as the Excitation Element (1200) and the Sensing Element (1300) are positioned close to each other, and that the Finger (5) is located close to both the Excitation Element (1200) and the Sensing Element (1300), the impedances (110, 130) are not uncorrelated. On the contrary, as the Impedance (110) increases—the fewer field lines from the Excitation Element (1200) will reach the Finger (5) and thus relatively more field lines from the Excitation Element (1200) will reach the Sensing Element (1300).

Accordingly, as the Impedance (110) decreases—the more field lines from the Excitation Element (1200) will reach the Finger (5) and thus relatively fewer field lines from the Excitation Element (1200) will reach the Sensing Element (1300).

Thus the Impedance (130) is modulated in response to modulation of the Finger Impedance (110). The electrical model for this is shown in FIG. 11, showing multiple Excitation Elements (1200, 1210, 1220, 1230, 1240, 1250) and multiple Sensing Elements (1300, 1310, 1320, 1330, 1340, 1350).

Comparing to FIG. 8 we observe that the Input Impedances (140-145) have disappeared, and that the Output Impedances (130-135) have become variable, as a result of the removal of the Sensor Elements (120-125).

Figure 12:
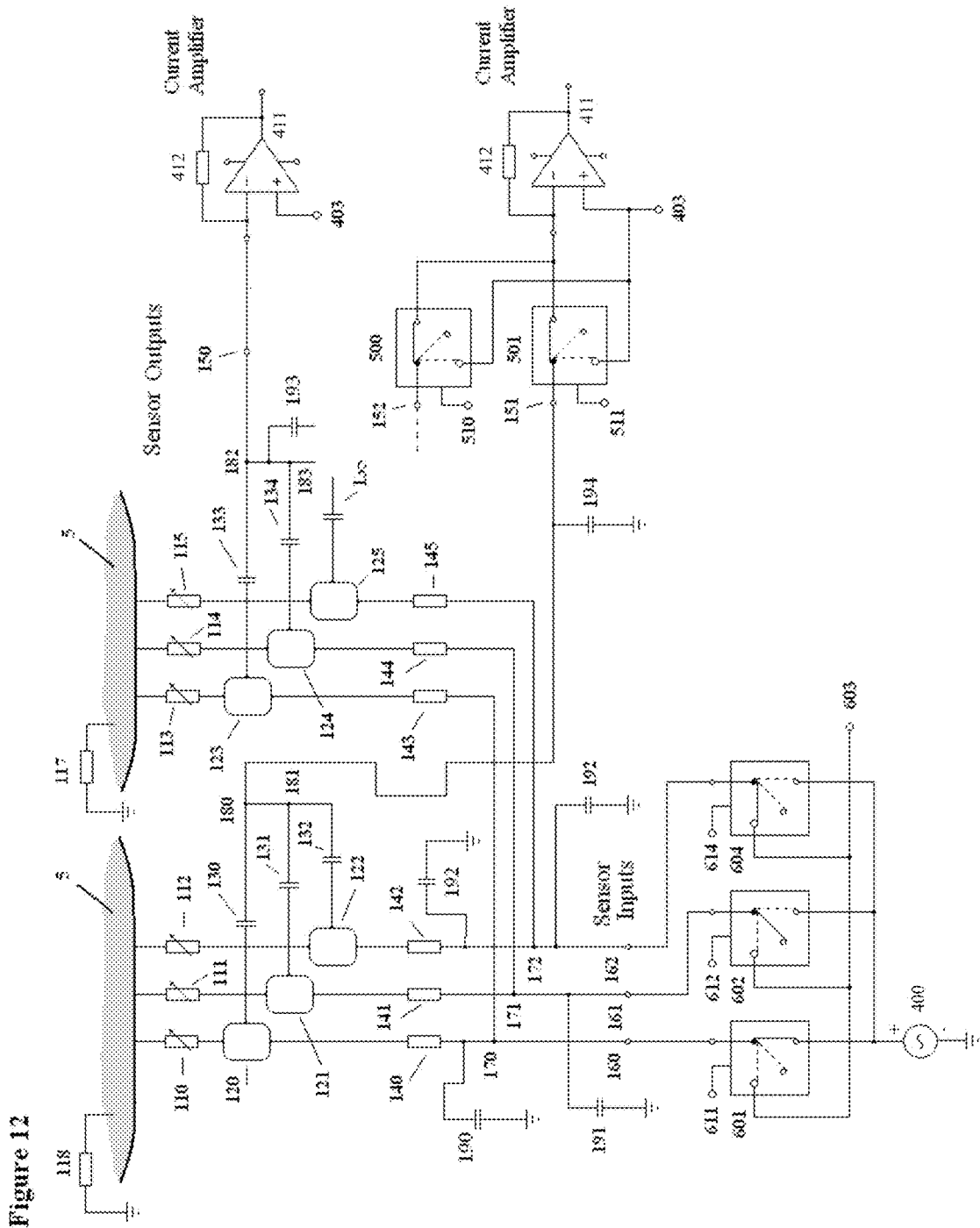
FIG. 12 is a schematic illustration of the present invention including a Sensor Area with six Sensor Elements as well as excitation and detection means, including Parasitic Output Capacitances of the Sensor Area. Furthermore Switching Elements are shown both on the Sensor Inputs and on (one of the) Sensor Outputs.

FIG. 12 is a schematic illustration of the present invention including a Sensor Area with six Sensor Elements as well as excitation and detection means, including Parasitic Output Capacitances of the Sensor Area. Furthermore Switching Elements are shown both on the Sensor Inputs and on (one of the) Sensor Outputs. Further details are described below in the context of FIG. 14.

Figure 13:
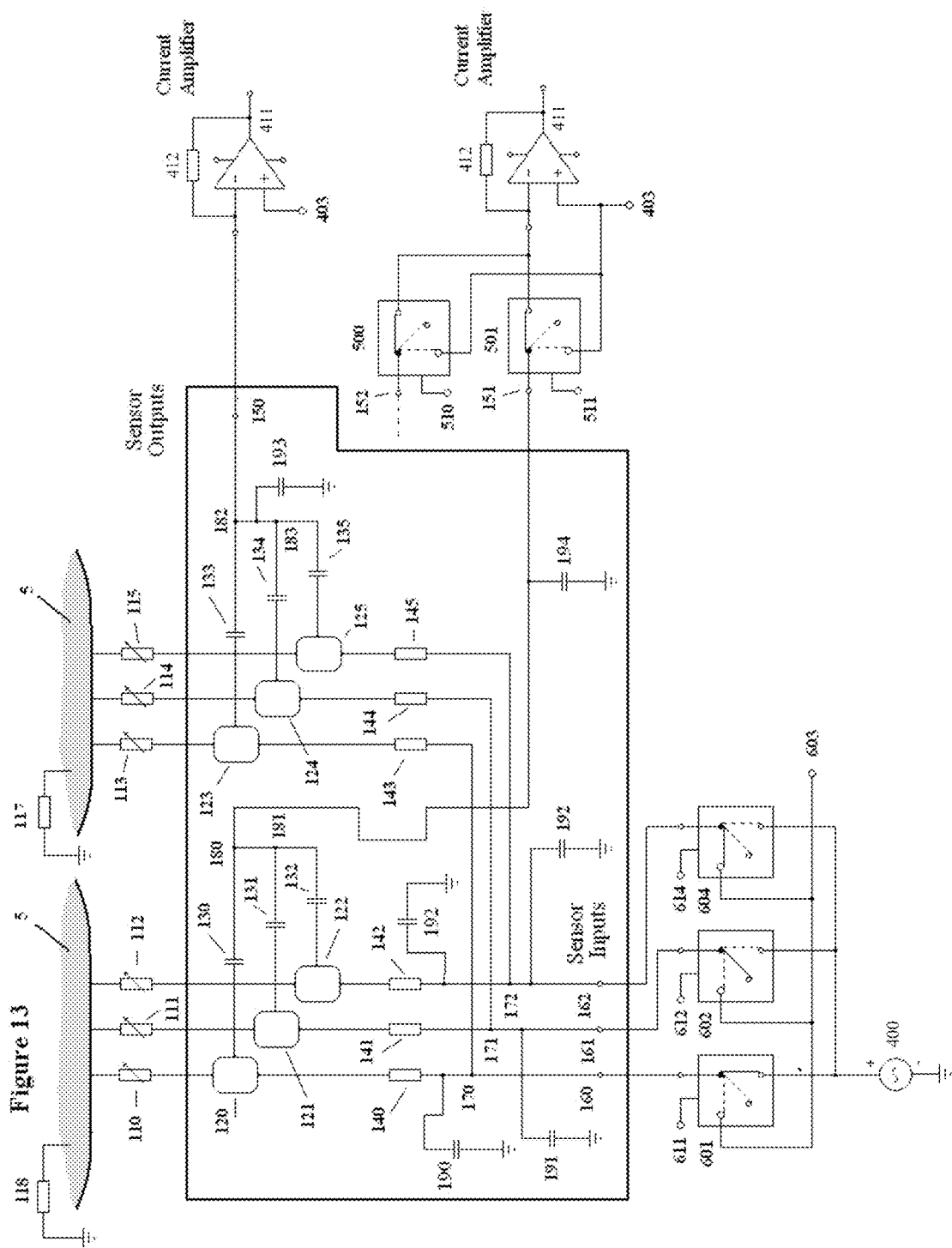
FIG. 13 is a schematic illustration of the present invention showing one way to partition the sensor of the current invention.

FIG. 13 is a schematic illustration of the present invention indicating one possible way to partition the sensor, in which the Sensor Area (1) is the portion included within the solid line in the figure. Further details are described below in the context of FIG. 14.

Figure 14:
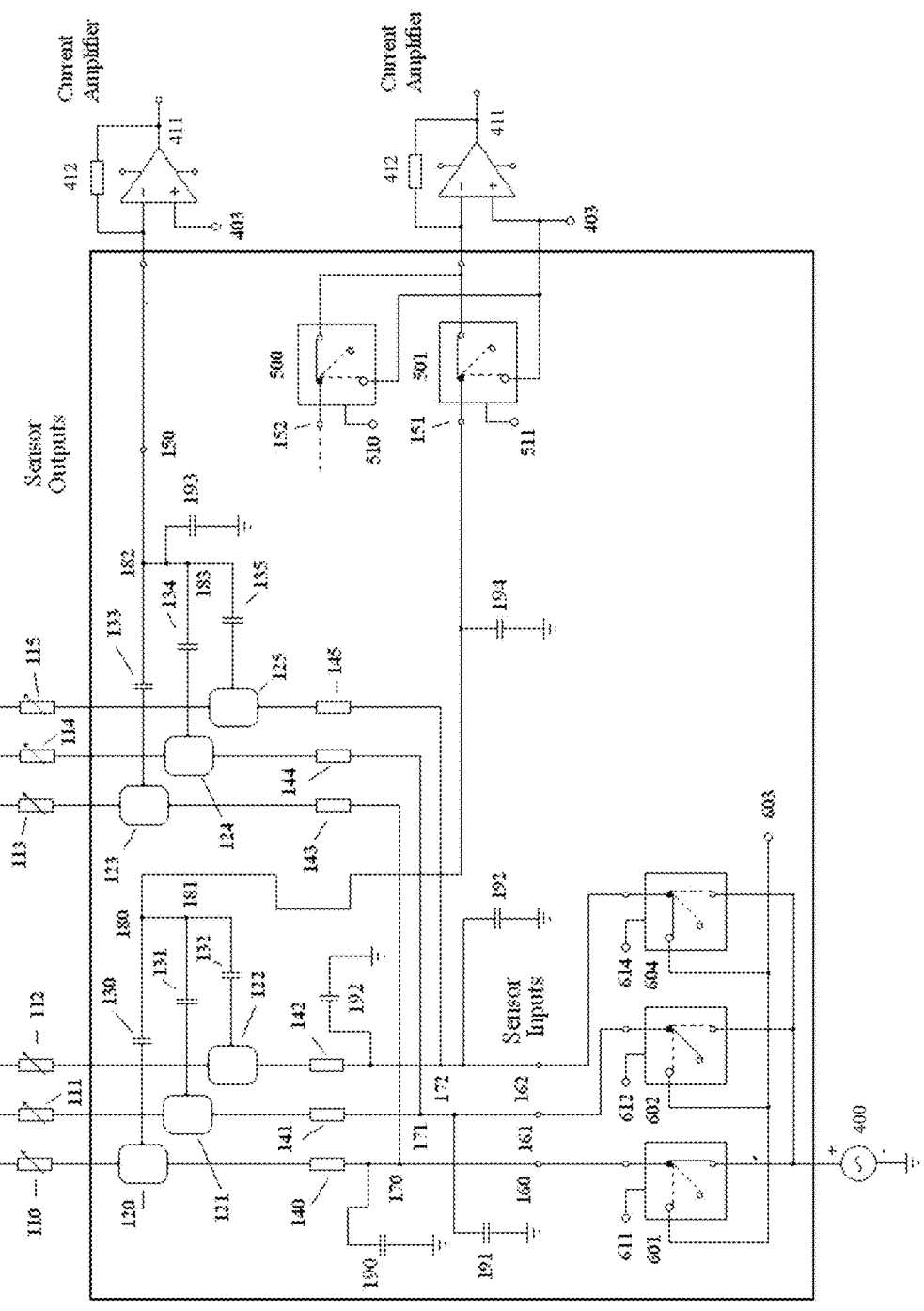
FIG. 14 is a schematic illustration of the present invention showing another way to partition the sensor of the current invention.

FIG. 14 is a schematic illustration of the present invention indicating another possible way to partition the Sensor, in which the Sensor Area (1) is the portion included within the solid line in the figure. We observe that in this way to partition the sensor the interface to the Electronic Circuit (4) would require the control signal (510, 511) for the Switches (500, 501) as well as the control signal (611, 612, 614) to the Switches (601, 602, 604) would need to be transferred to the Sensor Area (1). The Switches may in that case be produced in the same manufacturing process as the one used for the Sensor Area (1), or they can be produced in a separate process and subsequently connected electrically to the Sensor Area (1). Switches (601, 602, 604) include an input signal at 603. The Electronic Circuit further includes Current Amplifiers (411) with feedback impedance (412) and with the positive input of the amplifier connected to ground (403) as described above.

Furthermore—(although not illustrated in any figure)—finally the complete sensor including Sensor Area (1), Carrier (2), Connection Means (3) and Electronic Circuit (4) can eventually be produced in the same manufacturing process, providing the benefits of reduced number of sensor interconnections—that is Sensor Outputs and Sensor Inputs of the present invention.

Figure 15:
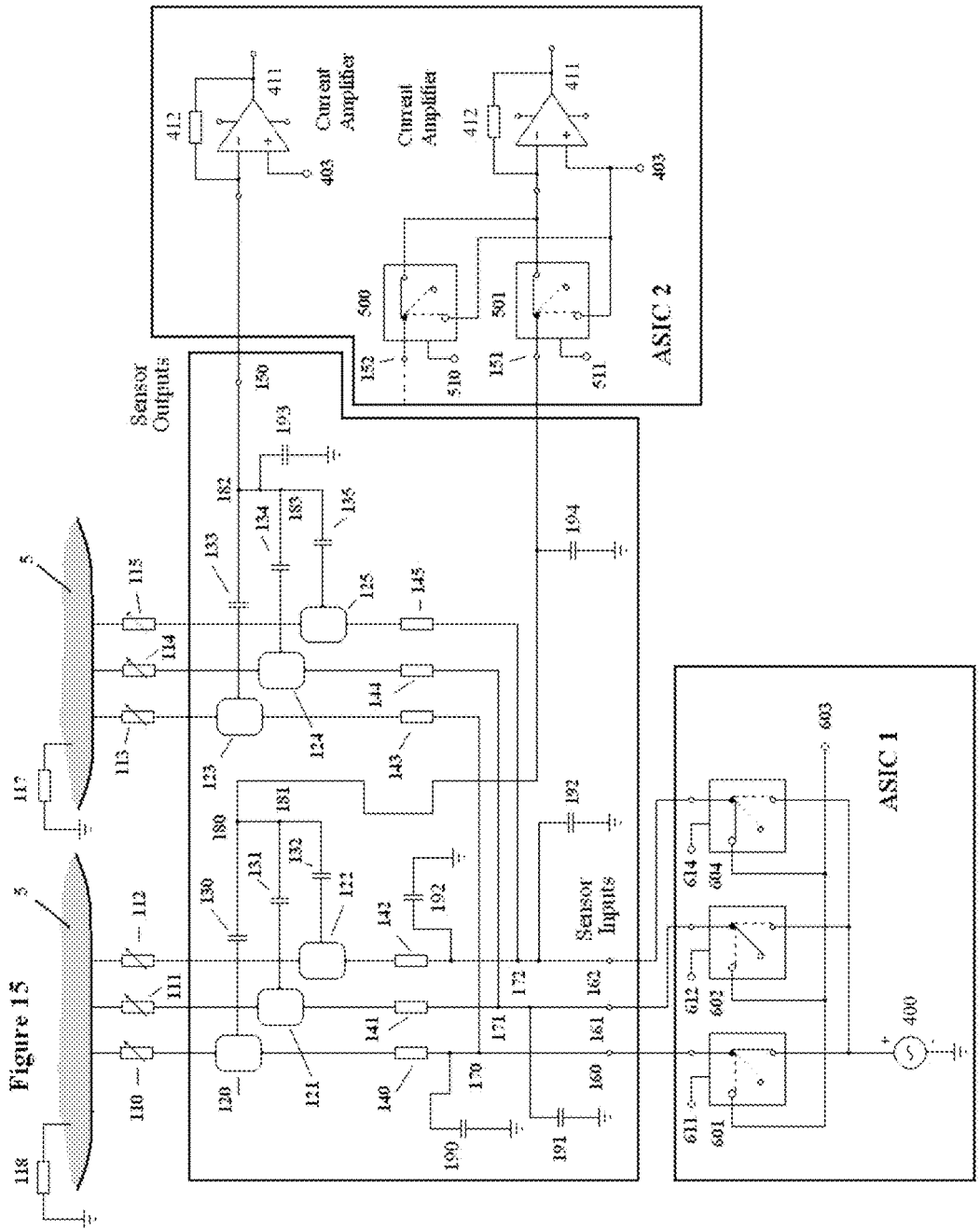
FIG. 15 is a schematic illustration of the present invention showing another way to partition the sensor of the current invention.

FIG. 15 is a schematic illustration of the present invention indicating another possible way to partition the Sensor including two the Electronic Circuits. One Electronic Circuit, denoted ASIC 1 is connected to the Sensor Inputs, whereas another Electronic Circuit, denoted ASIC 2 is connected to the Sensor Outputs. Obviously, the two Electronic Circuits would need to have communication or control signals (not shown) between each Electronic Circuit allowing the Electronic Circuit to coordinate the overall detection process. Or, in the absence of such control or communication signals the Electronic Circuits in other ways need to be able to obtain a desired functionality, for instance by being able to respond to control signals from other sources.

The invention claimed is:

1. A sensor for detection of a characteristic of an object, wherein the sensor is configured for concurrent detection of a plurality of sensor elements and is electrically connected to an electronic circuit; the sensor comprising:
   a sensor surface adapted to accommodate the object for detection of the characteristic of the object;
   at least one sensor electrode located in a first position on the sensor surface, the at least one sensor electrode being configured to detect the characteristic of the object;
   a first excitation element electrically coupled to the at least one sensor electrode via a first impedance;
   a sensor input electrically connected to the first excitation element;
   a voltage or current source electrically connected to the sensor input and configured to provide a voltage or current signal;
   a first sensing element electrically coupled to the at least one sensor electrode via a second impedance;
   a first sensor output electrically connected to the first sensing element; and
   a first current amplifier electrically connected to the first sensor output;
   wherein a reference voltage is supplied by the electronic circuit to the first current amplifier, the reference voltage further being provided to the first sensor output by the first current amplifier; and wherein the at least one sensor electrode is configured to provide an output current via the first sensing element to the first sensor output, the output current being determined by the characteristics in response to the voltage or current signal.

2. The sensor according to claim 1, wherein the sensor further comprises:
- at least one second sensor electrode located in a second position different from the first position;
- a second excitation element electrically coupled to the second sensor electrode via a third impedance, the second excitation element further being electrically connected to the sensor input;
- a second sensing element electrically coupled to the second sensor electrode via a fourth impedance;
- a second sensor output electrically connected to the second sensing element; and
- a second current amplifier electrically connected to the second sensor output, the second current amplifier providing the reference voltage to the second sensor output;
- wherein the second sensing element is configured to provide a second output current to the second sensor output, the second output current at any given time being determined by the characteristics in response to the voltage or current signal, and at the same given time the second output current is unaffected by the first output current and the first output current is unaffected by the second output current.

3. The sensor according to claim 1, wherein the sensor further comprises:
- at least one second sensor electrode located in a second position different from the first position;
- a second excitation element electrically coupled to the second sensor electrode via a third impedance;
- a second sensor input electrically connected to the second excitation element;
- a second reference voltage electrically connected to the second sensor input; and
- a second sensing element electrically connected to the second sensor electrode via a fourth impedance, the second sensing element being electrically connected to the first sensor output;
- wherein the second sensing element is configured to provide a second output current to the first sensor output such that the second output current at any given time is essentially zero and the first output current at the same given time is unaffected by the second output current.

4. The sensor according to claim 1, further comprising:
- multiple sensor inputs;
- multiple sensor outputs; and
- multiple sensor electrodes, the number of sensor electrodes being essentially equal to the product of the number of sensor inputs and the number of sensor outputs.

5. The sensor according to claim 1, further comprising:
- a second reference voltage supplied by the electronic circuit;
- a first input switching element electrically connected to the first sensor input, the first switching element being controlled by the electronic circuit and configured to electrically connect the first sensor input to the voltage or current source, leave the first sensor input electrically floating, and electrically connect the first sensor input to the second reference voltage;
- a second input switching element; and
- at least one second sensor input electrically connected to the second switching element;
- wherein the second switching element is controlled by the electronic circuit and is configured to electrically connect the second sensor input to the voltage or current source, leave the second sensor input floating, and electrically connect the second sensor input to the second reference voltage.

6. The sensor according to claim 1, further comprising:
- a first output switching element electrically connected to the first sensor output and configured to electrically connect the first sensor output to the current amplifier, leave the first sensor output electrically floating, and electrically connect the first sensor output to the reference voltage;
- a second output switching element; and
- at least one second sensor output electrically connected to the fourth switching element;
- wherein the fourth switching element is configured to electrically connect the second sensor output to the current amplifier, leave the second sensor output electrically floating, and electrically connect the second sensor output to the reference voltage.

7. The sensor according to claim 1, wherein the first excitation element is positioned beneath the at least one sensor electrode and the first sensing element is positioned beneath the at least one sensor electrode.

8. A sensor for detection of a characteristic of an object, wherein the sensor is configured for concurrent detection of a plurality of sensor elements and is electrically connected to an electronic circuit; the sensor comprising:
- a sensor surface configured to accommodate the object;
- a first excitation element provided on the sensor surface;
- a first sensor input electrically connected to the first excitation element;
- a voltage or current source electrically connected to the first sensor input and configured to provide a voltage or current signal;
- a first sensing element provided on the sensor surface;
- wherein the first excitation element and the first sensing element are configured to form an excitation-sensing pair for mutual detection of the characteristics;
- a first sensor output electrically connected to the first sensing element;
- a reference voltage supplied by the electronic circuit to the first sensor output; and
- a first current amplifier electrically connected to the first sensor output, the current amplifier providing the reference voltage to the first sensor output;
- wherein the excitation-sensing pair is positioned on the sensor surface and adapted to provide a first output current to the first sensor output, the first output current being determined by the characteristics in response to the voltage or current source; and
- multiple sensor inputs;
- multiple sensor outputs; and
- multiple excitation-sensing pairs, the number of excitation-sensing pairs being equal to the product of the number of sensor inputs and the number of sensor outputs.

9. The sensor according to claim 8, further comprising:
- at least one second excitation-sensing pair comprising:
  - a second sensing element; and
  - a second excitation element electrically coupled to the second sensing element via an impedance, the second excitation element further being electrically connected to the first sensor input;
- a second sensor output electrically connected to the second sensing element; and a second current amplifier electrically connected to the second sensor output, the second current amplifier providing the reference voltage to the second sensor output;

wherein the second sensing element is adapted to provide a second output current to the second sensor output, the second output current at any given time being determined by the characteristics in response to the voltage or current signal, and at the same given time the second output current is unaffected by the first output current and the first output current is unaffected by the second output current.

10. The sensor according to claim 8, further comprising:
at least one second excitation-sensing pair comprising:
   a second sensing element; and
   a second excitation element electrically coupled to the second sensing element via an impedance;
a second sensor input electrically coupled to the second excitation element;
a second reference voltage electrically connected to the second sensor input;
a second sensing element electrically connector to the sensor output;
wherein the second sensing element is configured to provide a second output current to the first sensor output such that the second output current at any given time is essentially zero and the first output current at the same given time is unaffected by the second output current.

11. The sensor according to claim 8, further comprising:
a second reference voltage supplied by the electronic circuit;
a first input switching element electrically connected to the first sensor input, the first switching element being controlled by the electronic circuit and configured to electrically connect the first sensor input to the voltage or current source, leave the first sensor input electrically floating, and electrically connect the first sensor input to the second reference voltage;
a second input switching element; and
at least one second sensor input electrically connected to the second switching element;
wherein the second switching element being controlled by the electronic circuit and configured to electrically connect the second sensor input to the voltage or current source, leave the second sensor input floating, and electrically connect the second sensor input to the second reference voltage.

12. The sensor according to claim 8, further comprising:
a first output switching element electrically connected to the first sensor output and configured to electrically connect the first sensor output to the current amplifier, leave the first sensor output electrically floating, and electrically connect the first sensor output to the reference voltage;
a second output switching element; and
at least one second sensor output electrically connected to the fourth switching element;
wherein the fourth switching element is configured to electrically connect the second sensor output to the current amplifier, leave the second sensor output electrically floating, and electrically connect the second sensor output to the reference voltage.

* * * * *